United States Patent [19]

Liang

[11] Patent Number: 4,593,042

[45] Date of Patent: Jun. 3, 1986

[54] BICYCLO-SUBSTITUTED PHENYLACETONITRILE DERIVATIVES

[75] Inventor: Chi-Dean Liang, Glenview, Ill.

[73] Assignee: G. D. Searle & Co., Skokie, Ill.

[21] Appl. No.: 789,255

[22] Filed: Oct. 18, 1985

[51] Int. Cl.$^4$ .................. A61K 31/275; C07C 121/78
[52] U.S. Cl. ..................................... 514/523; 558/408
[58] Field of Search ..................... 260/465 E; 514/523

[56] References Cited

U.S. PATENT DOCUMENTS 3,261,859 7/1966 Dengel ........................... 260/465 E
4,438,131 6/1984 Ehrmann et al. .................. 424/278

Primary Examiner—Dolph H. Torrence
Attorney, Agent, or Firm—Steven M. Odre

[57] ABSTRACT

The invention relates to compounds of the formula:

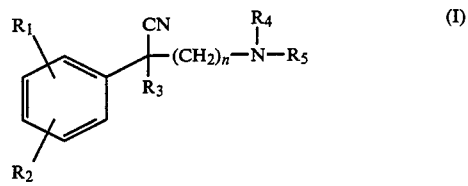

which are useful cardiovascular agents.

10 Claims, No Drawings

BICYCLO-SUBSTITUTED PHENYLACETONITRILE DERIVATIVES

BACKGROUND OF THE INVENTION

The present invention provides novel compounds of formula I:

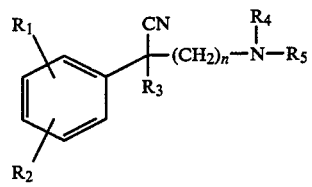

which are pharmacologically useful as cardiovascular agents and, particularly, as antihypertensive, anti-anginal and calcium channel blocking agents with minimal adverse cardiac effects.

The invention further relates to novel pharmaceutical compositions comprising one or more of the active compounds of the invention utilized in conjunction with suitable pharmaceutical carriers as well as methods of using such compounds and pharmaceutical compositions thereof in the treatment, prophylaxis, or mitigation of cardiovascular diseases or conditions, such as hypertension and angina.

The compounds of formula I comprise substituted phenylacetonitrile (or benzeneacetonitrile) derivatives wherein an alkyl aminoalkylene chain is attached to the carbon atom bearing the cyano function and the amino group thereof is substituted by a hydrogenated bicyclic aromatic substituent. The hydrogenated bicyclic aromatic substituent characterizing the compounds of formula I represents a major departure from previously suggested phenylacetonitrile derivatives which require the presence of a phenyl (or substituted phenyl) alkyl amino group as the moiety on the right side of the molecule.

For example, U.S. Pat. No. 3261859 discloses α[3-[[2-(3,4-dimethoxyphenyl)ethyl]methylamino]propyl]-3,4-dimethoxy-α-(1-methylethyl)hydrochloride) (i.e., verapamil hydrochloride) as a coronary vasodilator.

U.S. Pat. No. 4438131 discloses diphenyl-azaalkane derivatives of the formula:

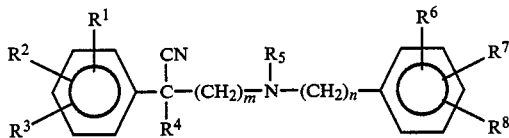

in which $R_1$, $R_2$, $R_3$, $R_6$, $R_7$, and $R_8$ are identical or different and selected from hydrogen, halogen, hydroxyl, trifluoromethyl, $C_1$-$C_4$ alkyl, nitro, $C_1$-$C_4$ alkoxy or $C_1$-$C_4$ alkyl mercapto and radicals in adjacent positions can together form methylenedioxy, ethylenedioxy, or 1,3 dioxatetramethylene groups; $R_4$ is straight-chain or branched-saturated or unsaturated alkyl of 9 to 20 carbon atoms, $R_5$ is hydrogen or $C_1$-$C_4$ alkyl and salts thereof. Anipamil[2-(3-methoxyphenyl)-2-[3-[N-[2-(3-methoxyphenyl)ethyl]methylamino]-propyl]tetradecanenitrile)] is disclosed within the foregoing patent and has subsequently been found to possess calcium ion antagonist activity analogous to verapamil hydrochloride.

SUMMARY OF THE INVENTION

The present invention relates to compounds of formula I:

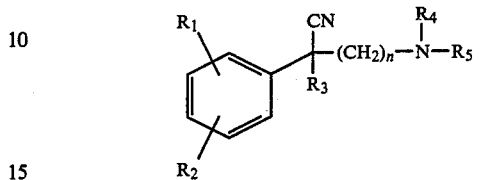

wherein $R_1$ and $R_2$ are the same or different and each is selected from hydrogen, halo, $C_1$-$C_4$ alkyl, $C_1$-$C_4$ alkoxy or trifluoromethyl;

$R_3$ is selected from straight or branched chain alkyl or alkenyl of from about 1 to 15 carbon atoms or of from about 2 to 15 carbon atoms, respectively;

$R_4$ is selected from hydrogen or $C_1$-$C_4$ alkyl;

$R_5$ is a bicyclic group selected from

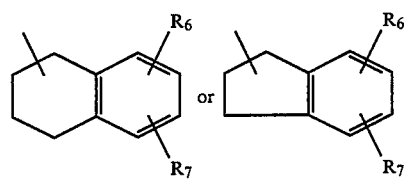

wherein $R_6$ and $R_7$ are the same as defined above for $R_1$ and $R_2$; and n is an integer from 2 to 4, inclusive, and the pharmaceutically acceptable nontoxic salts and hydrates thereof.

It is, therefore, an object of the present invention to afford novel cardiovascularly active compounds of formula I.

It is a further object of the present invention to provide methods for obtaining antihypertensive and calcium antagonist effects in mammals by the administration of preselected dosages of active compounds of formula I or pharmaceutically acceptable salts and stereoisomers thereof in appropriate nontoxic pharmaceutical dosage unit forms or compositions.

A still further object of the present invention is to provide dosage unit forms adapted for oral or parenteral administration and useful in the treatment, management, and mitigation of hypertensive conditions or disorders and other cardiovascular conditions where calcium channel blockade is therapeutically advantageous.

DETAILED DESCRIPTION OF THE INVENTION

It has now been found, in accordance with the present invention, that these and other similar objects, advantages, and features are accomplished according to the products, compositions, and methods of the invention comprising compounds of formula I.

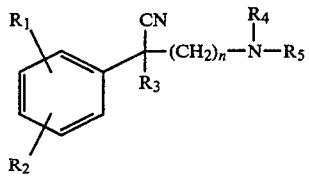

wherein $R_1$ and $R_2$ are the same or different and each is selected from hydrogen, halo, $C_1$-$C_4$ alkyl, $C_1$-$C_4$ alkoxy or trifluoromethyl;

$R_3$ is selected from straight or branched chain alkyl or alkenyl of from about 1 to 15 carbon atoms; or of from about 2 to 15 carbon atoms, respectively;

$R_4$ is selected from hydrogen or $C_1$-$C_4$ alkyl;

$R_5$ is a bicyclic group selected from

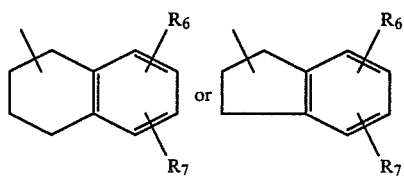

wherein $R_6$ and $R_7$ are the same as defined above for $R_1$ and $R_2$; and n is an integer from 2 to 4, inclusive, and the pharmaceutically acceptable nontoxic salts and hydrates thereof.

As used throughout the present specification and claims, the expressions "alkyl" and "alkoxy" are inclusive of straight and branched chain carbon-carbon linkages, e.g. methyl, ethyl, n-propyl, isopropyl, n-butyl, isobutyl, tert-butyl, etc. having the number of carbon atoms specified. The term "alkenyl" includes straight or branched chain unsaturated carbon-carbon linkages such as propenyl, 2-pentenyl, butenyl, nonenyl, dodecenyl, etc. The term "halo" includes chloride, flourine, bromine, and iodine with chlorine being preferred. The expression "pharmaceutically acceptable non-toxic salts" as used herein is intended to include those salts capable of being formed with the present compounds and substituted derivatives thereof in accordance with the invention without materially altering the chemical structure or pharmacological properties of the parent compounds. Representative of preferred salt forms include the hydrochloride, citrate, and maleate salts.

It will also be appreciated by those skilled in the art that the compounds of the present invention may exist in their optically active enantiomeric forms and racemic mixtures thereof and such stereoisomeric forms are specifically encompassed within the compounds of formula I.

Representative of preferred compounds of formula I for use in the pharmaceutical compositions and methods of the present invention are those of the following formula II.

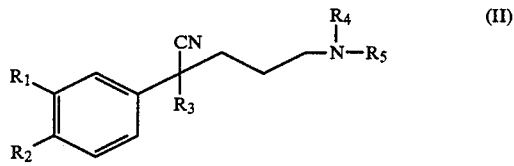

wherein $R_1$ and $R_2$ are either both hydrogen or $C_1$-$C_4$ alkoxy (preferably methoxy);

$R_3$ is $C_1$-$C_{12}$ alkyl (preferably isopropyl);

$R_4$ is $C_1$-$C_4$ alkyl (preferably methyl) and $R_5$ is:

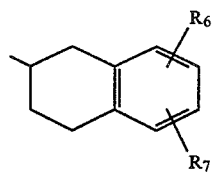

wherein $R_6$ and $R_7$ are the same or different and independently selected from hydrogen or $C_1$-$C_4$ alkoxy (preferably methoxy).

Especially preferred compounds of formula II are

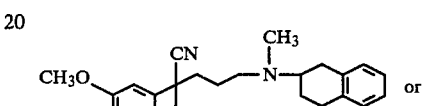

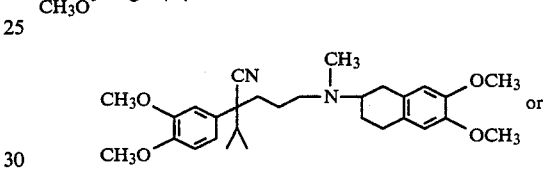

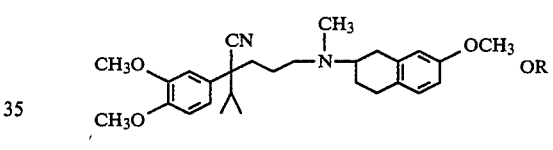

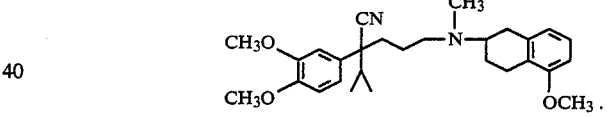

The compounds of the present invention may be prepared in accordance with previously employed methods for the synthesis of phenylacetonitrile derivatives and modifications thereof to obtain the $R_1$, $R_2$, $R_3$, $R_4$, and $R_5$ substituents thereon as defined above. In general, an appropriately substituted β-tetralone is converted to a substituted amino Tetralin ® derivative (i.e., 1,2,3,4-tetrahydronaphthalenamine). A phenylacetonitrile reactant bearing a leaving group thereon (for example, halogen) of the general formula III is then prepared:

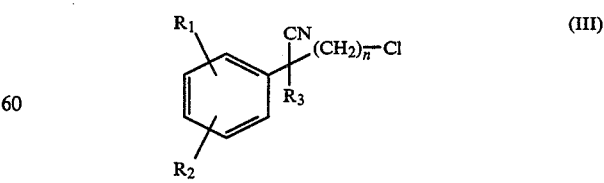

The phenyl acetonitrile of formula III is reacted under appropriate conditions with the previously prepared amino Tetralin derivative. The foregoing reaction is depicted as follows:

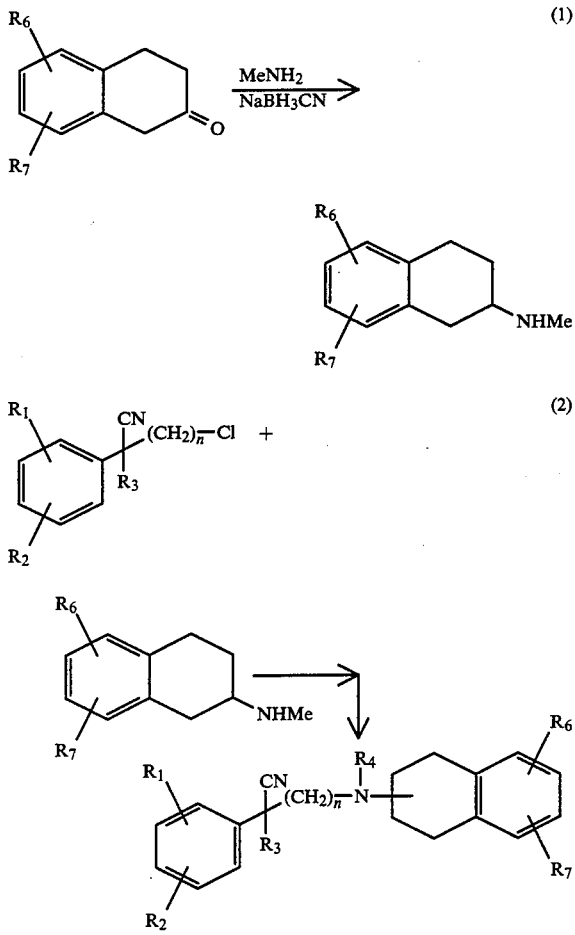

(1)

(2)

The following nonlimiting examples are afforded in order that those skilled in the art may more readily understand the present invention and specific preferred embodiments thereof with respect to the preparation of starting materials, intermediates and compounds in accordance with the foregoing description. All temperatures are degrees Celsius unless otherwise specified.

EXAMPLE 1

1,2,3,4-Tetrahydro-5-methoxy-N-methyl-2-naphthalenamine

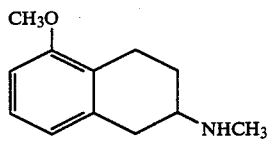

To 5-methoxy-β-tetralone (1.54 g, 9 mmol) in 30 ml of methanol was added 1.8 g of methylamine hydrochloride (25 mmol) portionwise. NaBH$_3$CN (1.3 g, 20 mmol) was added during 1 h. and the mixture was stirred at room temperature for 48 h.

The reaction mixture was quenched with water dropwise, followed by the addition of dilute NH$_4$OH solution until the mixture became alkaline. Methanol was removed in vacuo and the organic material was extracted into 40 ml of ether. Acidic extraction followed by basification and extraction into ether yielded, after solvent removal, the title product as a yellow-brown oil (0.95 g, 65%).

NMR(CDCl$_3$): δ(ppm),1.30–2.20(m, 3H), 2.50(s, 3H), 2.6–3.2(m, 4H), 3.78(s, 3H), 6.50–7.20(m, 3H). The hydrochloride salt of the title product was prepared by dissolving 0.6 g of the above oil in 20 ml of diethylether and adding concentrated HCl acid in isopropanol (25% by weight) until slightly acidic. The precipitate was filtered, washed with diethyl ether and dried at 60° C. to yield 0.62 g of the hydrochloride salt (mp 203°–205° C.).

Analysis: Calc'd (%): C, 63.29, H, 7.97, N, 6.15. Found (%): C, 63.25, H, 7.77, N, 6.12.

The following tetrahydronapthalenamine derivatives were prepared according to the procedure of Example 1 using appropriate starting materials.

EXAMPLE 2

1,2,3,4-Tetrahydro-N-methyl-2-naphthalenamine, monohydrochloride

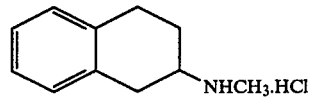

Analysis: Calc'd (%): C, 66.83, H, 8.16, N, 7.08. Found (%): C, 66.83, H, 8.06, N, 7.06.

NMR(CDCl$_3$): δ(ppm), 1.42–2.20(m, 3H), 2.42(s, 3H), 2.50–3.20(m, 4H), 7.00 (5H).

EXAMPLE 3

1,2,3,4-Tetrahydro-6,7-dimethoxy-N-methyl-2-naphthalenamine

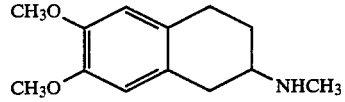

NMR(CDCl$_3$): 1.40–2.20(m, 3H), 2.40(s, 3H), 2.45–3.20(m, 4H), 3.72(s, OH), 6.58(s, 2H).

EXAMPLE 4

1,2,3,4-Tetrahydro-7-methoxy-N-methyl-2-naphthalenamine

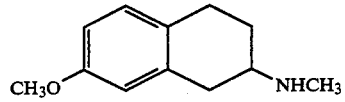

NMR(CDCl$_3$): 1.42–2.30(m, 3H), 2.50(s, 3H), 2.55–3.20(m, 4H), 3.85(s, 3H), 6.60–7.20(m, 3H).

EXAMPLE 5

1,2,3,4-Tetrahydro-6-methoxy-N-methyl-2-naphthalenamine

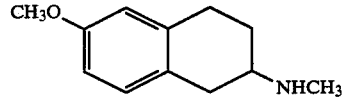

NMR(CDCl$_3$): 1.30–2.20(m, 3H), 2.40(s, 3H), 2.60–3.20(m, 4H), 3.71(s, 3H), 6.50–7.10(m, 3H).

EXAMPLE 6

Isopropyl Veratryl Cyanide

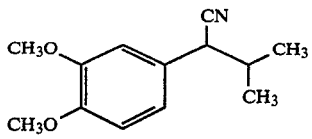

27.83 g of 50% NaOH solution, 5.84 g (145.95 mmol) of NaOH pellets and veratryl cyanide (8.9 g, 50.24 mmol) were placed in a 100 ml round-bottom flask. 2.05 g (9.02 mmol) of TEBAC was added and the mixture was stirred until homogenous while heating to 50° C. with a heating mantle. Isopropyl bromide (5.5 ml, 58.58 mmol) was added dropwise over 0.5 h at 50° C.±5° to the above mixture which was stirred at 50° C.±5° for 24 hours. The reactin mixture was partitioned between water and toluene and transferred to a separatory funnel. The aqueous layer was drawn off and extracted with ether. The toluene and ether fractions were combined and washed twice with water and dried over $Na_2SO_4$. The mixture was filtered and solvent removed by rotary evaporation. The combined fractions, following evaporation and recrystallization from 70 percent methanol/water yielded 6.32 g of the title compound (57% yield).

NMR ($CDCl_3$): δ (ppm), 0.71-1.3(m, 6H), 1.9-2.3(m, 1H), 3.59(d, J=6 Hz, 1H), 3.87(s, 6H), 6.75-7.0(m, 3H).

EXAMPLE 7

α-(3-chloropropyl)-3,4-dimethoxy-α-(1-methylethyl)-phenylacetonitrile

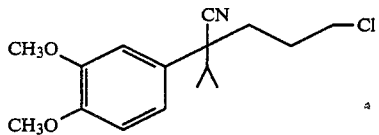

Diisopropylamine (3 ml) in 50 ml of tetrahydrofuran (THF) was cooled to −78° C. and 12.5 ml of n-butyl lithium was added dropwise while stirring. After 15 min., 4.4 g (20 mmol) of dimethoxyphenyl isopropyl acetonitrile in 20 ml of anhydrous THF was added dropwise during 10 min. The mixture was stirred at −78° C. for 0.5 h. before 3-bromopropyl chloride (2.2 ml, 3.14 g) was added dropwise and the mixture stirred at −78° C. for 15 min. then allowed to warm to room temperature and stirred for 1 h. The mixture was cooled to 0° C. and 10 ml of water was added dropwise. THF was removed in vacuo and the organic material was extracted into $CHCl_3$. After solvent removal, the residue was subjected to column chromatography. Elution with EtOAc/Skellysolve B(5:95) yielded 770 mg of unreacted starting material and 3.0 g of the desired product (68% yield) as an oil.

NMR($CDCl_3$): δ (ppm) 0.84 (d, J=6 Hz, 3H), 1.22 (d, J=6 Hz, 3H), 1.3-2.5 (m, 5H), 3.30-3.70 (m, 2H), 3.8 (s, 6H), 6.8-7.0 (m, 3H).

EXAMPLE 8

3,4-dimethoxy-α-(1-methylethyl)-α-[3-[N-methyl-N-(1,2,3,4-tetrahydro-2-naphthalenyl)amino]propyl]-phenylacetonitrile, citrate (1:1) (SC43131)

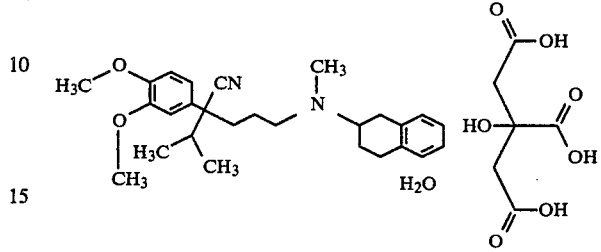

To the product of Example 2 (0.6 g-mmol) and the alkylchloride of Example 7 (0.9 g, 3 mmol) in 15 ml of dimethyl formamide was added $Na_2CO_3$(0.6 g) and the mixture was heated overnight at 80° C.

The reaction mixture was then cooled to room temperature, 50 ml of diethyl ether added, washed with water (20 ml×3) and dried over $MgSO_4$. Following filtration and removal of solvent in vacuo, a brown oil was obtained which was submitted to column chromatography yielding 0.4 g (30%) of the desired product.

NMR ($CDCl_3$), δ (ppm): 0.8 (d, J=3.2 Hz, 3H), 1.18 (d, J=3.2 Hz, 3H), 2.28 (s, 3H), 1.8-3.0 (m, 13H), 3.84 (s, 3H), 3.85 (s, 3H), 6.8-7.4 (m, 7H).

The citrate salt of the title compound was prepared by dissolving the brown oil obtained above in 20 ml of diethylether and adding a saturated solution of citric acid in diethyl ether until the resulting solution was slightly acidic. The precipitate which formed was collected and washed with ether (10 ml×3) to give the citrate salt.

Analysis: Calc'd (%): C, 64.69, H, 7.24, N, 4.57. Found (%): C, 65.01, H, 7.33, N, 4.74.

Utilizing procedures analogous to those of Examples 7 and 8, the following compounds were prepared.

EXAMPLE 9

3,4-dimethoxy-α-(1-methylethyl)-α-[3-[N-methyl-N-(1,2,3,4-tetrahydro-6,7-dimethoxy-2-naphthalenyl)amino]propyl]phenylacetonitrile, citrate (1:1) (SC43123)

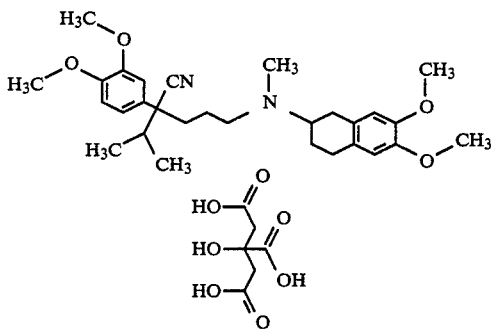

Analysis: Calc'd (%): C, 62.49, H, 7.19, N, 4.16. Found (%): C, 62.29, H, 7.35, N, 4.17.

EXAMPLE 10

3,4-dimethoxy-α-(1-methylethyl)-α-[3-[N-methyl-N-(1,2,3,4-tetrahydro-6-methoxy-2-naphthalenyl)amino]-propyl]phenylacetonitrile, citrate (1:1) (SC43197)

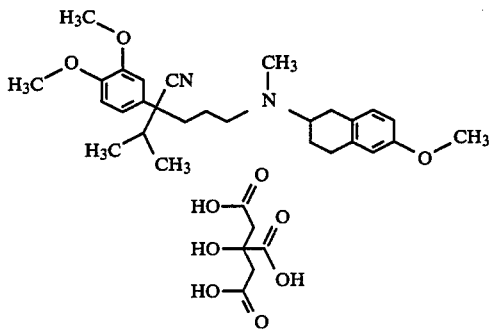

Analysis: Calc'd (%): C, 63.54, H, 7.21, N, 4.36. Found (%): C, 64.00, H, 7.04, H, 4.39.

EXAMPLE 11

3,4-dimethoxy-α-(1-methylethyl)-α-[3-[N-methyl-N-(1,2,3,4-tetrahydro-5-methoxy-2-naphthalenyl)amino]-propyl]phenylacetonitrile, citrate (1:1) (SC43995)

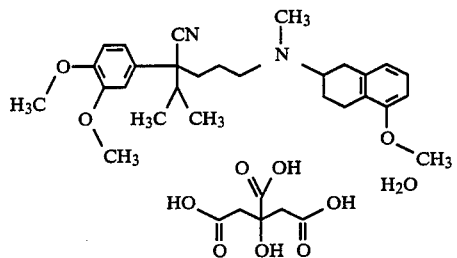

Analysis: Calc'd (%): C, 61.80, H, 7.32, N, 4.24. Found (%): C, 61.25, H, 7.04, N, 4.09.

EXAMPLE 12

3,4-dimethoxy-α-(1-methylethyl)-α-[3-[N-methyl-N-(1,2,3,4-tetrahydro-7-methoxy-2-naphthalenyl)amino]-propyl]phenylacetonitrile, citrate (1:1) (SC43996)

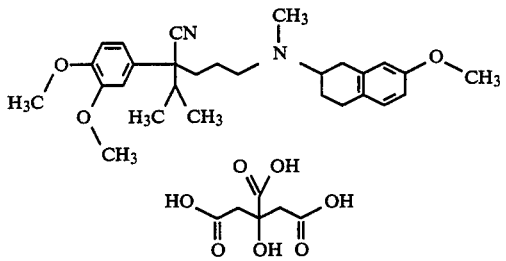

Analysis: Calc'd (%): C, 63.54, H, 7.21, N, 4.36. Found (%): C, 63.03, H, 7.22, N, 4.61.

PHARMACOLOGICAL EVALUATIONS

The compounds of this invention exhibit antihypertensive activity as determined in the unanesthetized spontaneously hypertensive rate (SHR) assay and/or exhibit calcium ion antagonism as demonstrated in isolated thoracic aorta segments from male spontaneously hypertensive rats. The test procedures employed to measure these activities are described below.

ANTI-HYPERTENSIVE ACTIVITY

Male, unanesthetized spontaneously hypertensive rats (SHR), 11 to 16 weeks old were used in this test procedure. The compounds to be tested were administered intragastrically at a dose of 50 mg/kg or intravenously at doses of 0.1 to 10 mg/kg.

Initial mean arterial blood pressure was measured directly via a previously implanted arterial catheter immediately before administration of the test compound. Blood pressure readings were made at hourly intervals, 24 hours per day, for 3 days following oral administration of the test compound and at 5, 10, and 15 minutes following intravenous administration. A compound was rated active if the mean post treatment blood pressure of treated rats was significantly different (p less than or equal to 0.05) than that of the control group concurrently administered placebo. Statistical comparisons were made using the analysis of variance test with two sided probability calculations.

The spontaneously hypertensive rat exhibits a genetically-linked hypertension that is similar in most respects to essential hypertension in man. Guanethidine, Apresoline, Aldomet, Clonidine, and Captopril are active in the foregoing hypertensive rat assay and are clinically useful antihypertensive agents.

CALCIUM ANTAGONISM IN VASCULAR SMOOTH MUSCLE

Isolated thoracic aortic rings from the male SHR were utilized in this test procedure.

The excised aortic ring was mounted in a tissue bath containing modified Kreb's solution. After depolarization of the tissue with potassium chloride (100 mM), calcium in cumulative concentrations of $1 \times 10^{-3}$M, $3.2 \times 10^{-3}$M, and $1 \times 10^{-2}$M was injected into the bath to produce vascular smooth muscle contraction. The developed tension (in grams) was measured and control dose-response values obtained. After one hour of incubation with a test compound at $1 \times 10^{-6}$M concentration, the same doses of calcium ions were repeated. The log dose-response curves of the control and after treatment were analyzed by linear regression. The pA2 value was calculated as a measure of calcium antagonism of the test compound. See Van Rossum, J. M. Arch. Int. Pharmacodyn, 143, 299–330, 1963. A compound was considered active as a vascular calcium antagonist if the pA2 was 6.0 or greater.

Calcium ions play an essential role in induction and maintenance of vascular smooth muscle contractility. In potassium depolarized vascular smooth muscle, calcium antagonists may block the entry of calcium ions into the cell or act by other mechanisms to inhibit the contractions induced by calcium ions. The inhibition of calcium ion-induced contraction of vascular smooth muscle is used to test compounds for vascular calcium antagonism. Cardiovascular diseases such as arrhythmias, angina-pectoris, hypertension, and peripheral vascular disease may be causally related to abnormalities in cellular handling of calcium ions. Calcium antagonists/entry blockers have been proven to be of value in the treatment of the aforementioned cardiovascular diseases or conditions. Verapamil, nifedipine, diltiazem and other drugs are active in the foregoing test and have, likewise, been demonstrated to be clinically useful cardiovascular agents.

The results obtained in the foregoing tests with respect to certain preferred compounds in comparison to verapamil are set forth in Table I below.

TABLE I

| Compound Example No. | SHR-mmHg intravenous (mg/kg) | $pA_2$ Ca++Antagonism |
|---|---|---|
| 8. | −30 at 0.1 mg/kg | 7.3 |
| 9. | −30 at 3.0 mg/kg | 6.9 |
| 10. | −24 at 3.0 mg/kg | 7.6 |
| 11. | −29 at 1.0 mg/kg | 7.3 |
| 12. | −20 at 1.0 mg/kg | 7.4 |
| verapamil | −30 at 0.3 mg/kg | 7.8 |

In further biology studies, the compound of Example 8 in the conscious SHR upon oral administration at 50 mg/kg/day for three days produced an antihypertensive effect persisting longer than 24 hours compared to 14 hours for verapamil. At 10 mg/kg/day orally administered for three days in the SHR, the compound of Example 8 produced an antihypertensive effect lasting approximately 12 hours, whereas the same dose of verapamil was effective for 6 hours. In the SHR model, it has also been found that administration of the compounds of the invention produced no increase in heart rate. Based upon these studies, the compounds of the present invention have been shown to be orally active in the SHR model with a longer duration of action than verapamil and that the desired antihypertensive effect is not accompanied by tachycardia.

In studying the antihypertensive effects of the compounds of the present invention using anesthetized beagle dogs, i.v. administration of the compounds of the present invention, verapamil and diltiazem resulted in approximately the same maximum hypotensive effect. However, the slope of the dose-blood pressure response curve was not as steep with the compound of the present invention (Example 8) compared to verapamil and diltiazem, suggesting that the blood pressure lowering effect of the present compounds is more predictable and, accordingly, safer than with comparative prior art compounds.

With respect to cardiac safety, the compounds of the present invention had a less depressant effect on atrial-ventricular conduction then verapamil or diltiazem. For example, the compound of Example 8 was found to have a more favorable therapeutic ratio for atrial-ventricular block and bradycardia than verapamil or diltiazem. The ratio of the dose required to slow or block atrial-ventricular conduction to the dose required to lower arterial pressure by 20 mmHg was 4 for the compound of Example 8 and 1 and 0.53 for verapamil and diltiazem, respectively. The ratio of the dose to decrease heart rate to the dose to lower arterial pressure was 3.1 for the compound of Example 8 and 1 and 0.53 for verapamil and diltiazem, respectively. The cardiac safety demonstrated by these results with respect to the compounds of the present invention represents a distinct advantage with respect to the ultimate usefulness of the present compounds as cardiovascular agents.

Reduction in arterial blood pressure is effected by decreasing total peripheral resistance as a result of arteriolar vasodilation produced by antagonism of calcium ions at the arteriols. The compounds of the present invention as shown in Table I are calcium channel blocking agents. In addition, the compounds of the invention also block the uptake of calcium ions into cultured vascular smooth muscle cells and antagonize the binding on nitrendipine to the calcium receptor in cardiac membranes.

Based upon these and other properties, the compounds of formula I are effective cardiovascular agents with ultimate therapeutic utility in angina, congestive heart failure, hypertension and other similar peripheral vascular disorders or conditions.

The compounds of the present invention can be administered in such oral dosage forms as tablets, capsules, pills, powders, granules, elixers, or syrups. Likewise, they may also be administered intravascularly, intraperitoneally, subcutaneously, or intramuscularly using forms known to those of ordinary skill in the pharmaceutical arts. In general, the preferred form of administration is oral. An effective but non-toxic amount of the compound is employed in the treatment of hypertension or to promote calcium antagonism, anti-anginal effects, etc. with resultant cardiovascular improvement. The dosage regimen utilizing the compounds of the present invention is selected in accordance with a variety of factors including the type, age, weight, sex, and medical condition of the patient; the severity of the condition to be ameliorated; the route of administration; and the particular compound employed or mixtures thereof. An ordinarily skilled physician can readily determine and prescribe the effective amount of the drug required to prevent, treat or arrest the progress of the condition. Dosages of the compounds of the present invention, when used for the indicated cardiovascular effects (e.g. hypotensive, anti-anginal or calcium antagonist effect) will range between about 0.1 mg/kg to about 10.0 mg/kg. The foregoing dosage ranges on a weight basis correspond to a total daily dosage in the average adult patient of between about 10 mg/day to 300 mg/day. Advantageously, the compounds of the present invention may be administered in a single daily dose. Of course, should it be necessary or desirable, the total daily dosage may be administered in equal divided doses three or four times daily.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweetners, natural and synthetic gums and such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the mammal treated, severity of hypertension, angina, etc., dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A compound of the formula

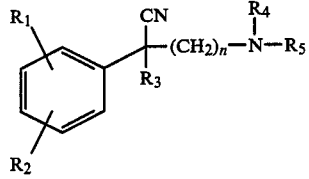

and the pharmaceutically acceptable salts and hydrates thereof wherein
- $R_1$ and $R_2$ are the same or different and each is selected from hydrogen, halo, $C_1$-$C_4$ alkyl, $C_1$-$C_4$ alkoxy or trifluoromethyl;
- $R_3$ is selected from straight or branched chain (a) alkyl of from about 1 to 15 carbon atoms or (b) alkenyl of from about 2 to 15 carbon atoms;
- $R_4$ is selected from hydrogen or $C_1$-$C_4$ alkyl;
- $R_5$ is a bicyclic group selected from

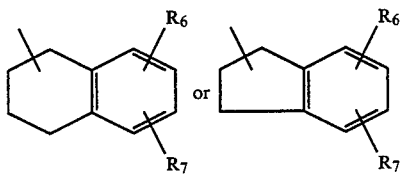

wherein $R_6$ and $R_7$ are the same as defined above for $R_1$ and $R_2$; and
n is an integer from 2 to 4, inclusive.

2. A compound according to claim 1, wherein said compound is of the formula

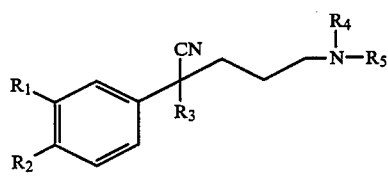

wherein $R_1$ and $R_2$ are either both hydrogen or both $C_1$-$C_4$ alkoxy; $R_3$ is $C_1$-$C_{12}$ alkyl; $R_4$ is $C_1$-$C_4$ alkyl; and $R_5$ is a group of the formula

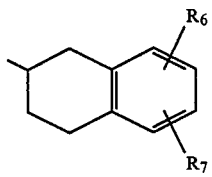

wherein $R_6$ and $R_7$ are the same or different and independently selected from hydrogen or $C_1$-$C_4$ alkoxy.

3. A compound according to claim 1, wherein said compound is selected from

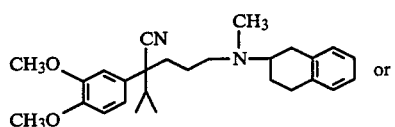

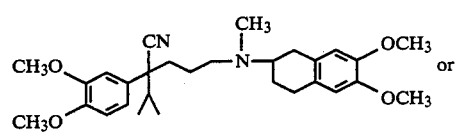

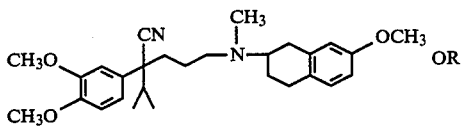

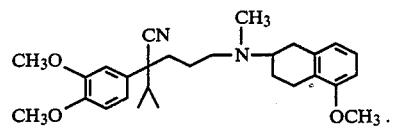

4. A compound according to claim 3, wherein said compound is of the formula

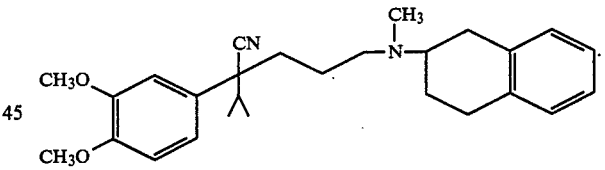

5. A pharmaceutical composition for promoting a calcium ion antagonist or antihypertensive effect in a mammal in need thereof comprising a pharmaceutical carrier and an effective amount of a compound according to claim 1.

6. A pharmaceutical composition according to claim 5, wherein said compound is of the formula

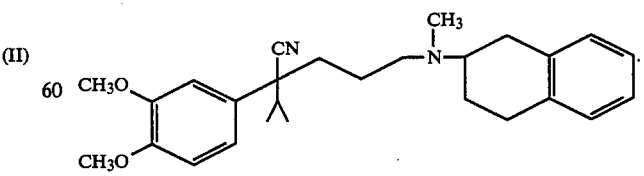

7. A method of promoting a calcium ion antagonist or antihypertensive effect in a mammal in need thereof comprising administering thereto an effective amount of a compound according to claim 1.

8. A method according to claim 7, wherein said compound is administered orally.
9. A method according to claim 7 wherein said compound is of the formula
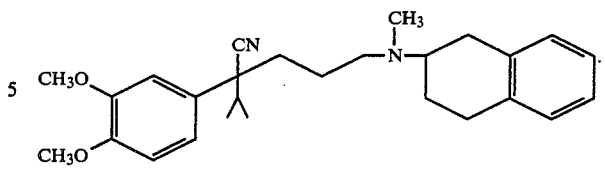
10. A method according to claim 7, wherein said compound is administered in combination with a pharmaceutical carrier.
* * * * *